US008862212B2

(12) United States Patent
Otto et al.

(10) Patent No.: US 8,862,212 B2
(45) Date of Patent: Oct. 14, 2014

(54) AGGREGATING CARDIAC RESYNCHRONIZATION THERAPY DATA

(75) Inventors: Helen W. Otto, Forest Lake, MN (US); Kevin T. Ousdigian, Shoreview, MN (US); Julian Sanchez, Shoreview, MN (US); Sean R. Landman, Minneapolis, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 13/316,177

(22) Filed: Dec. 9, 2011

(65) Prior Publication Data

US 2013/0110834 A1 May 2, 2013

Related U.S. Application Data

(60) Provisional application No. 61/553,725, filed on Oct. 31, 2011.

(51) Int. Cl.
*A61B 5/0402* (2006.01)
*G06F 19/00* (2011.01)

(52) U.S. Cl.
CPC .................................. *G06F 19/3443* (2013.01)
USPC ........................................................ 600/513

(58) Field of Classification Search
USPC ................................................. 600/508, 513
See application file for complete search history.

(56) References Cited

U.S. PATENT DOCUMENTS

| 6,907,289 B2 | 6/2005 | Stahmann et al. |
| 2005/0137629 A1 | 6/2005 | Dyjach et al. |
| 2011/0022981 A1* | 1/2011 | Mahajan et al. ............. 715/810 |

OTHER PUBLICATIONS

Ousdigian et al., "Reduced Bi-Ventricular Pacing is Associated with Decreased Survival in 10,830 CRT-D Patients with AF," PowerPoint Presentation, May 13, 2010, 14 pp.
Koplan et al., "Heart Failure Decompensation and All-Cause Mortality in Relation to Percent Biventricular Pacing in Patients with Heart Failure," Journal of the American College of Cardiology, vol. 53, No. 4, Jan. 27, 2009, pp. 355-360.
Hayes et al., "Cardiac resynchronization therapy and the relationship of percent biventricular pacing to symptoms and survival," Heart Rhythm, vol. 8, No. 9, pp. 1469-1475, Sep. 2011.
Borek et al., "Impact of AF on Mortality in 51,058 Patients with CRT-D," PowerPoint Presentation, May 13, 2010, 18 pp.
U.S. Appl. No. 13/297,104, by Sean R. Landman, filed Nov. 15, 2011.

* cited by examiner

*Primary Examiner* — Amanda Patton
(74) *Attorney, Agent, or Firm* — Michael C. Soldner

(57) ABSTRACT

Cardiac resynchronization therapy (CRT) performance data for a number of patients in which an implantable medical device (IMD) is implanted is aggregated and reports of the aggregated data are generated, e.g., for review by organizations or individual clinicians treating the patients. In one example, a method includes collecting CRT performance data correlated to cardiac rhythm event data for a first group of patients in which an IMD configured to deliver CRT is implanted, aggregating, with a computing device, the CRT performance data correlated to the cardiac rhythm event data for a second group of patients from among the first group of patients, and generating, with the computing device, a report comprising the aggregation of the CRT performance data correlated to the cardiac rhythm event data for the second group of patients.

34 Claims, 8 Drawing Sheets

| Patient Data | | | | | Clinical Data | | |
|---|---|---|---|---|---|---|---|
| Patient Name | Serial # | Device Brand | Session Duration (days) | Transmission Date | CRT Pacing (%) | Time in AT/AF (%) | CRT Pacing During AT/AF (%) |
| Patient 1 | PVR026301H | Concerto | 55 | 12/28/2010 | OFF | 0.0 | |
| Patient 2 | PVR028565H | Concerto | 108 | 2/25/2011 | 63.8 | 0.0 | 87.0 |
| Patient 3 | PZV003925H | Concerto II | 94 | 5/13/2011 | 76.7 | 100.0 | 76.7 |
| Patient 4 | PVR029268H | Concerto | 96 | 10/15/2008 | 83.3 | 100.0 | 83.3 |
| Patient 5 | PVR006172H | Concerto | 64 | 4/2/2009 | 83.3 | 26.7 | 42.2 |
| Patient 6 | PVR033641H | Concerto | 98 | 5/6/2011 | 84.0 | 100.0 | 84.0 |
| Patient 7 | PVR011905H | Concerto | 88 | 7/11/2011 | 84.1 | 0.0 | |
| Patient 8 | PVR042871H | Concerto | 48 | 10/7/2010 | 88.1 | 0.0 | |
| Patient 9 | PVR001765H | Concerto | 14 | 6/11/2010 | 88.4 | 100.0 | 88.4 |
| Patient 10 | PVR053345H | Concerto | 98 | 3/11/2011 | 88.8 | 4.4 | 64.7 |
| Patient 11 | PVR003039H | Concerto | 56 | 3/25/2010 | 89.1 | 0.0 | |
| Patient 12 | PVR017194H | Concerto | 94 | 4/29/2011 | 89.2 | 8.4 | 66.1 |
| Patient 13 | PVR008521H | Concerto | 98 | 11/19/2007 | 90.8 | No RA Lead | |
| Patient 14 | PZV003784H | Concerto II | 94 | 5/6/2011 | 91.0 | 0.1 | 60.0 |
| Patient 15 | PVR033863H | Concerto | 90 | 9/11/2008 | 91.2 | 56.4 | 91.7 |
| Patient 16 | PVR017960H | Concerto | 95 | 5/20/2011 | 91.5 | 0.0 | |
| Patient 17 | PVR027399H | Concerto | 91 | 11/26/2010 | 92.4 | 96.6 | 92.4 |
| Patient 18 | PVR008520H | Concerto | 291 | 5/19/2009 | 92.7 | 100.0 | 92.7 |

FIG. 5

| Patient Data | | Reason for Loss of CRT Pacing (%) | | | Programming Data | | | | | | | |
|---|---|---|---|---|---|---|---|---|---|---|---|---|
| Patient Name | Serial # | AT/AF | PVCs | Other* | Pacing Mode | SAV (ms) | PAV (ms) | Lower Rate (bpm) | Upper Tracking Rate (bpm) | Conducted AF Response | Atrial Tracking Recovery | V. Sense Response |
| Patient 1 | PVR026301H | | | | DDDR | 350 | 350 | 60 | 100 | ON | OFF | OFF |
| Patient 2 | PVR028565H | 0 | 21 | 79 | DDD | 150 | 180 | 50 | 120 | OFF | OFF | ON |
| Patient 3 | PZV003925H | 100 | 0 | 0 | DDD | 130 | 160 | 60 | 130 | ON | OFF | ON |
| Patient 4 | PVR029268H | 100 | 0 | 0 | VVIR | | | 80 | | OFF | | ON |
| Patient 5 | PVR006172H | 92 | 0 | 8 | DDDR | 180 | 210 | 70 | 130 | ON | OFF | OFF |
| Patient 6 | PVR033641H | 100 | 0 | 0 | DDDR | 100 | 130 | 60 | 130 | ON | OFF | ON |
| Patient 7 | PVR011905H | 0 | 1 | 99 | VVIR | | | 75 | | ON | | ON |
| Patient 8 | PVR042871H | 0 | 32 | 68 | DDD | 100 | 130 | 60 | 130 | ON | OFF | OFF |
| Patient 9 | PVR001765H | 100 | 0 | 0 | DDDR | 90 | 110 | 75 | 110 | ON | OFF | ON |
| Patient 10 | PVR053345H | 14 | 72 | 14 | DDD | 100 | 130 | 60 | 130 | ON | OFF | OFF |
| Patient 11 | PVR003039H | 0 | 1 | 99 | DDD | 100 | 150 | 70 | 130 | ON | OFF | ON |
| Patient 12 | PVR017194H | 27 | 1 | 72 | DDDR | 100 | 130 | 60 | 130 | ON | OFF | ON |
| Patient 13 | PVR008521H | No RA Lead | | | VVIR | | | 70 | | ON | | ON |
| Patient 14 | PZV003784H | 0 | 39 | 60 | DDD | 100 | 130 | 70 | 130 | ON | OFF | ON |
| Patient 15 | PVR033863H | 53 | 6 | 41 | DDDR | 100 | 130 | 70 | 120 | ON | OFF | ON |
| Patient 16 | PVR017960H | 0 | 24 | 76 | DDDR | 100 | 130 | 60 | 130 | ON | OFF | ON |
| Patient 17 | PVR027399H | 97 | 1 | 2 | DDIR | 130 | 130 | 70 | | ON | | ON |
| Patient 18 | PVR008520H | 100 | 0 | 0 | DDD | 100 | 130 | 70 | 130 | ON | OFF | OFF |

FIG. 6

CRT PERFORMANCE
INDIVIDUAL CLINIC REPORT
Summary
Number of Patients: 335
Patients with CRT Pacing off: 3
Patients with <95% CRT Pacing: 22%
CareLink data as of: 8-Apr-2011
Clinic 1 - Minneapolis
Minneapolis, MN
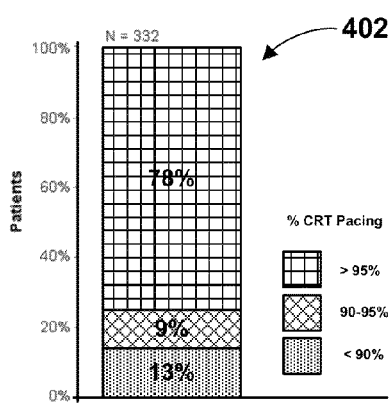
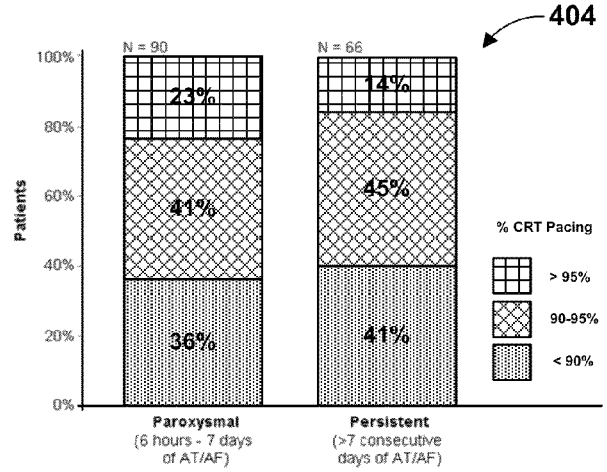
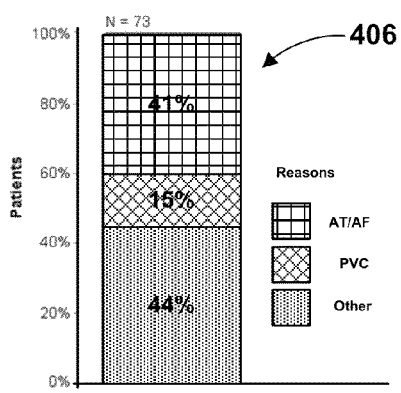
Programming
| CRT Pacing Feature | % On |
|---|---|
| Atrial Tracking Recovery | 48% |
| Conducted AF Response | 61% |
| V Sense Response | 76% |
FIG. 7

AGGREGATING CARDIAC RESYNCHRONIZATION THERAPY DATA

This application claims the benefit of U.S. Provisional Patent Application No. 61/553,725, filed Oct. 31, 2011, the entire content of which is incorporated herein by reference.

TECHNICAL FIELD

The disclosure relates to implantable medical devices, and, more particularly, to implantable medical devices configured to deliver cardiac stimulation therapy.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria. These depolarizations may not originate from the SA node, but may instead originate from an arrhythmogenic substrate, such as an ectopic focus, within the atrial heart tissue. The reduced pumping efficiency due to atrial fibrillation requires the ventricle to work harder, which is particularly undesirable in sick patients that cannot tolerate additional stresses. As a result of atrial fibrillation, patients must typically limit activity and exercise.

An even more serious problem, however, is the induction of rapid and irregular ventricular heart rhythms by the atrial fibrillation. Irregular atrial depolarization signals associated with atrial fibrillation are received by the AV node and may be conducted to ventricles. During atrial fibrillation, the intervals between ventricular depolarizations may be shortened and vary substantially. Such induced ventricular arrhythmias compromise pumping efficiency even more drastically than atrial arrhythmias. This phenomenon is referred to as rapidly conducted atrial fibrillation, or "conducted AF."

Patients with heart failure are, in some cases, treated with cardiac resynchronization therapy (CRT). CRT is a form of cardiac pacing. In some examples, CRT involves delivery of pacing pulses to both ventricles ("biventricular pacing") to synchronize their contraction. In other examples, CRT involves delivery of pacing pulses to one ventricle to synchronize its contraction with that of the other ventricular, such as pacing the left ventricle to synchronize its contraction with that of the right ventricle.

SUMMARY

Examples according to this disclosure are directed to aggregating CRT performance data for a number of patients in which an IMD is implanted, and generating reports of the aggregated data, e.g., for review by organizations or individual clinicians treating the patients. For example, CRT performance data may be aggregated for all of the patients receiving treatment from one location, e.g., a particular clinic. Additionally, the CRT performance data may be aggregated for patients from multiple locations, e.g., to aggregate regional or national CRT performance data. In one example, CRT performance data may be aggregated for multiple populations of patients and the data associated with each population may be compared to one another. For example, aggregated CRT performance data for a single clinic may be compared to averages for CRT performance for a number of populations of patients, e.g., nationwide data or to aggregated CRT performance data for high performing clinics. High performing clinics may be clinics with CRT performance data in the top 10% of all sampled clinics.

In one example, a method includes collecting CRT performance data correlated to cardiac rhythm event data for a first group of patients in which an IMD configured to deliver CRT is implanted, aggregating, with a computing device, the CRT performance data correlated to the cardiac rhythm event data for a second group of patients from among the first group of patients, and generating, with the computing device, a report comprising the aggregation of the CRT performance data correlated to the cardiac rhythm event data for the second group of patients.

In another example, a system includes a processor and a computer-readable storage medium storing instructions. The processor is configured to execute the instructions stored on the computer-readable storage medium to cause the processor to collect cardiac resynchronization therapy (CRT) performance data correlated to cardiac rhythm event data for a first group of patients in which an implantable medical device (IMD) configured to deliver CRT is implanted, aggregate the CRT performance data correlated to the cardiac rhythm event data for a second group of patients from among the first group of patients, and generate a report comprising the aggregation of the CRT performance data correlated to the cardiac rhythm event data for the second group of patients.

In another example, a system includes means for collecting cardiac resynchronization therapy (CRT) performance data correlated to cardiac rhythm event data for a first group of patients in which an implantable medical device (IMD) configured to deliver CRT is implanted, means for aggregating, with a computing device, the CRT performance data correlated to the cardiac rhythm event data for a second group of patients from among the first group of patients, and means for generating, with the computing device, a report comprising the aggregation of the CRT performance data correlated to the cardiac rhythm event data for the second group of patients.

In another example, a computer-readable storage medium comprising instructions that cause a programmable processor to collect cardiac resynchronization therapy (CRT) performance data correlated to cardiac rhythm event data for a first group of patients in which an implantable medical device (IMD) configured to deliver CRT is implanted, aggregate the CRT performance data correlated to the cardiac rhythm event data for a second group of patients from among the first group of patients, and generate a report comprising the aggregation of the CRT performance data correlated to the cardiac rhythm event data for the second group of patients.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 5-8 illustrate a number of reports of aggregated cardiac resynchronization therapy data that may be generated as part of the example method of FIG. 4.

DETAILED DESCRIPTION

Figure 1:
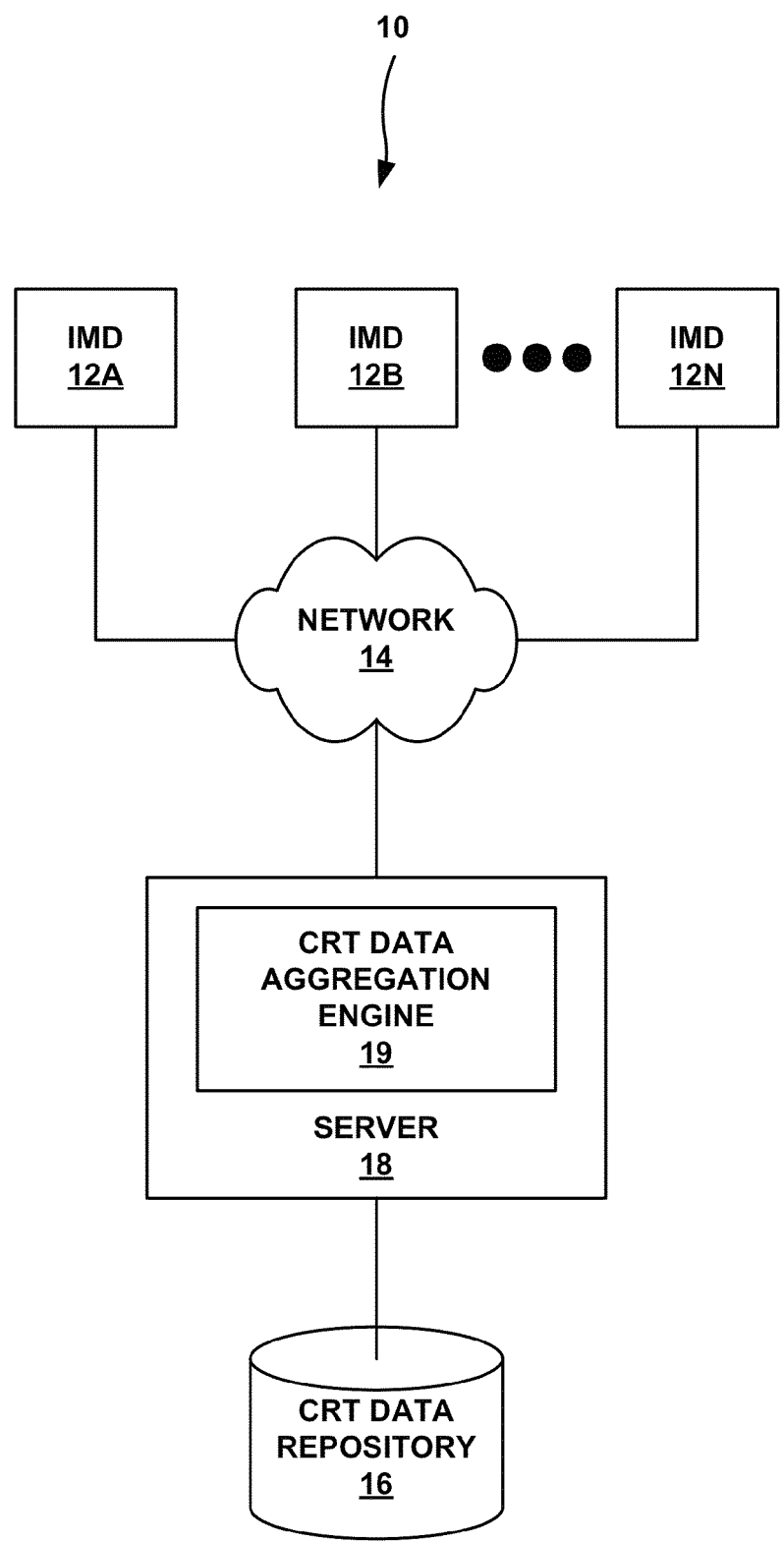
FIG. 1 is a conceptual diagram of an example system for aggregating cardiac resynchronization therapy data for a number of patients.

Cardiac resynchronization therapy (CRT) has known mortality and morbidity benefits for a subset of patients with heart failure. Additionally, the benefit of CRT is known to depend upon consistent delivery of the therapy. As such, CRT may be more effective as the percentage of ventricular contractions that are paced, and thereby synchronized, is increased. Generally speaking, therefore, it is desirable to deliver CRT to a patient receiving such treatment 100 percent of the time. In other words, it is generally desirable to synchronize 100 percent of the patient's ventricular contractions via CRT delivered by the IMD implanted in the patient. It has also been demonstrated that certain threshold levels of percentage CRT delivery, although below 100 percent, may nevertheless affect morbidity and mortality.

Although high percentages of CRT delivery is desirable, circumstances arise which preclude CRT delivery by an IMD. For example, in some cases, an atrial tachyarrhythmia, including atrial tachycardia or atrial fibrillation (hereinafter AT/AF) may increase ventricular contraction rates such that ventricular contraction occurs before expiration of the programmed escape interval, which, in this case is the programmed AV interval. The amount of loss of CRT therapy delivery is generally of such importance to the efficacy of CRT delivered to a patient, that it is very beneficial to provide visibility of CRT performance data to clinicians treating patients with CRT. Additionally, the utility of reporting data related to CRT delivery may be improved by presenting CRT performance data correlated to one or more possible causes for the loss of CRT delivery, e.g., percentage loss of CRT delivery correlated to a percentage of time the patient was in AT/AF.

Individual IMDs and/or IMD systems, e.g., including an IMD and an external programmer or patient monitor, may be configured to track and store CRT performance data for the IMD, e.g., including the percentage of time CRT delivery occurs and the corresponding percentage of loss of CRT delivery. Additionally, an IMD may monitor and store data that may form the basis for determining one or more causes for the loss of CRT delivery, e.g., the occurrence and duration of AT/AF. Thus, in some medical systems including an IMD implanted within a patient, a clinician may ascertain and analyze CRT performance data and review data related thereto for that IMD and patient, e.g., using an external programmer in local communication with the IMD.

In addition to having visibility to CRT performance data for individual patients, it may also be beneficial to view CRT performance data for an entire population of patients, e.g., all the patients treated at a single location like a clinic or a population of patients treated at multiple locations. For example, an organization or individual clinician may wish to be able to view and analyze CRT performance data for trends for all of the patients the organization or clinician is treating with CRT. However, because CRT performance data is only available on an individual patient basis, and because even this data may not be well organized or correlated to other related data, it may be difficult or impossible for interested parties to view and analyze CRT performance data for an entire population of patients in a meaningful and efficient manner.

In view of the importance of CRT performance data to patients, and the challenges with collecting, viewing, and analyzing such data, examples according to this disclosure are directed to aggregating CRT performance data for a number of IMDs implanted in a number of patients, and generating reports of the aggregated data, e.g., for review by organizations or individual clinicians treating the patients. In one example according to this disclosure, a method includes collecting CRT performance data correlated to cardiac rhythm event data for a first group of patients in which an implantable medical device (IMD) configured to deliver CRT is implanted, aggregating, with a computing device, the CRT performance data correlated to the cardiac rhythm event data for a second group of patients from among the first group of patients, and generating, with the computing device, a report comprising the aggregation of the CRT performance data correlated to the cardiac rhythm event data for the second group of patients.

For example, a method according to this disclosure may include collecting CRT performance data for a number of IMDs implanted in a number of patients correlated to one or more different types of cardiac rhythm events for those patients including, e.g., AT/AF, a premature ventricular contraction (PVC), or a ventricular sensing episode (VSE). A VSE may occur due to ventricular tachyarrhythmia, supraventricular tachyarrhythmia, conducted atrial tachyarrhythmia, an intrinsic rate above the programmed upper tracking rate, or any reason that may cause or allow ventricular depolarizations to occur before expiration of a programmed escape interval, e.g., programmed atrioventricular delay, for CRT pacing. Examples of VSEs include ventricular tachycardia (VT), ventricular fibrillation (VF), nonsustained tachycardia (NST), and other ventricular or supraventricular tachyarrhytmias. The CRT performance data correlated to AT/AF, PVC, and/or various types of VSEs may be received, e.g., from a data repository storing CRT performance and related data collected from a number of IMDs.

The data in the data repository may have previously been processed to correlate the CRT data to other relevant data, e.g., possible causes for CRT loss such as AT/AF, PVC, and/or various types of VSEs. The CRT performance data correlated to AT/AF, PVC, and/or various types of VSEs for each of the IMDs and patients may be aggregated for a particular population of devices and associated patients. For example, the CRT performance data correlated to AT/AF, PVC, and/or various types of VSEs may be aggregated for all of the patients that are treated at a particular clinic or by a particular physician. A report is generated that includes the aggregated CRT performance data correlated to AT/AF, PVC, and/or VSEs for all of the patients in the target population. Organizations and individual clinicians may view and analyze the report, e.g., to discern the percentage loss of CRT delivery for the patients, and the extent to which different causes contributed to the loss of CRT delivery.

For example, the report may indicate the percentage of loss of CRT delivery and a percentage contribution of each of AT/AF, PVC, and/or VSE to the total loss of CRT. For example, the report may indicate for one patient that of the total time over which CRT therapy was intended to be delivered there was actually 88.8% of CRT delivery. For the same patient, the report may also indicate that of the 21.2% loss of CRT delivery, 14% of the 21.2% loss of CRT delivery was correlated to AT/AF, 72% was correlated to PVC, and 14% was correlated to other types of cardiac rhythm events, including various types of VSEs. The same report may indicate the respective values of the foregoing variables related to CRT performance for a number of patients, e.g., all the patients treated at one clinic. The report may also indicate for the patients experiencing loss of CRT delivery, which also experienced AT/AF and what percentage of time over the total period of therapy delivery did the AT/AF occur. Additionally, the report may indicate what percentage of CRT delivery occurred during AT/AF for the patients experiencing this arrhythmia. In one example, the report also presents a correlation of CRT performance and/or the occurrence and duration of AT/AF to different outcomes, including, e.g., mortality, hospitalizations, and quality of life metrics. The particular manner in which CRT performance and related data is aggregated for a population of patients and reports thereof are generated is described in greater detail with reference to the following examples.

CRT performance data aggregation and reporting according to this disclosure may provide a number of advantages to organizations and individuals treating patients with CRT. CRT performance data aggregation and reporting according to this disclosure may provide an efficient mechanism by which an organization or individual may judge the quality of CRT provided to an entire population of patients. Additionally, the techniques described herein may allow interested parties to analyze the aggregated CRT performance data for trends regarding or causes of loss of CRT delivery and thereby formulate strategies for improving performance in the future. Organizations and individuals may also drill down from aggregated CRT performance data for an entire population of patients to a particular subset of patients. For example, organizations and individuals may drill down from aggregated CRT performance data for an entire population of patients to a subset of patients with below a threshold level of acceptable CRT performance, e.g., below a threshold level of percentage of CRT delivery or above a threshold level of loss of CRT delivery. By quickly and efficiently identifying the subset of patients with below a threshold level of acceptable CRT performance in this manner, interested parties may use the aggregated CRT performance data as an efficient triage tool for effectively responding to potentially harmful loss of treatment for certain patients.

Figure 2:
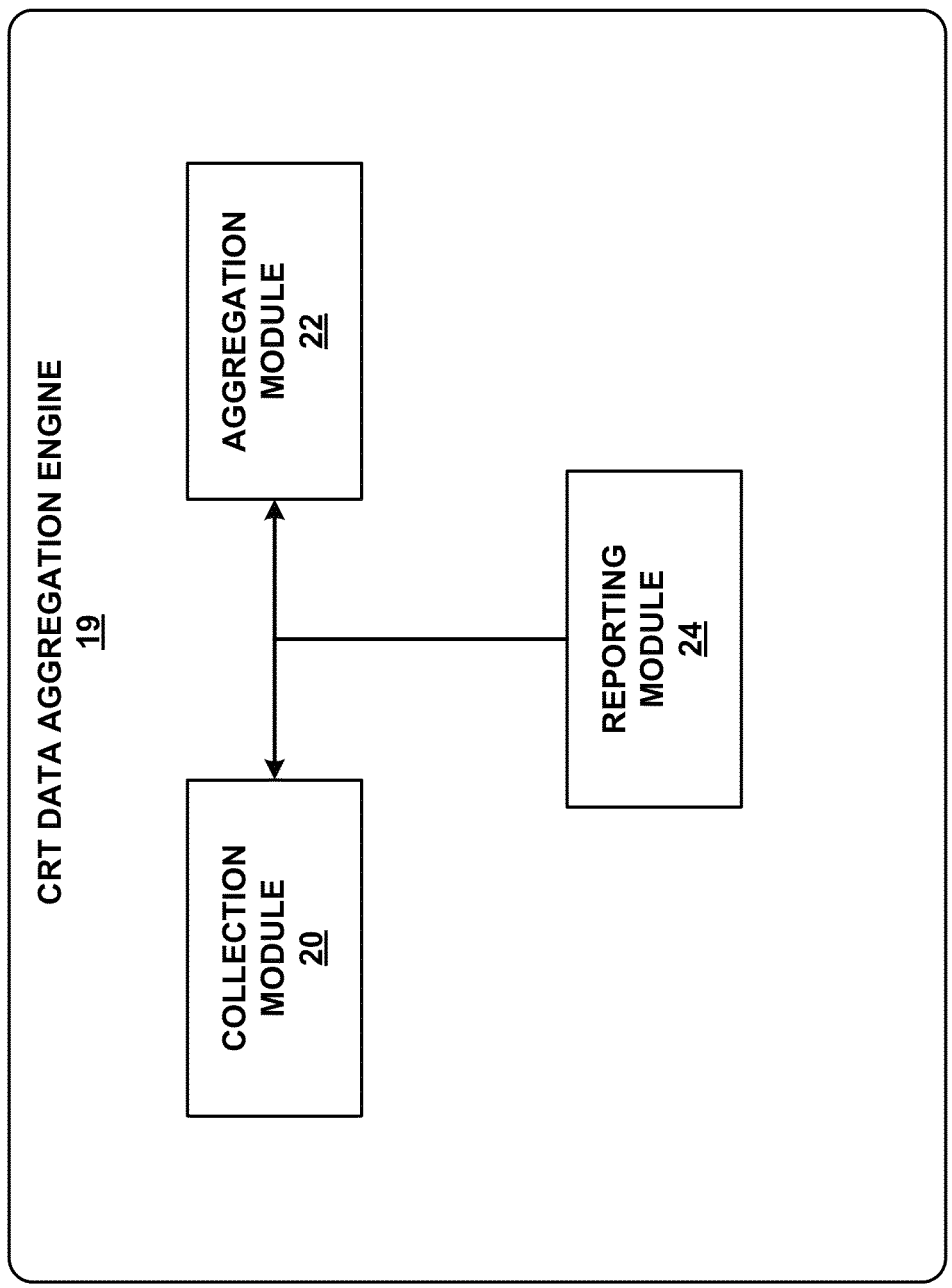
FIG. 2 is a block diagram illustrating an example cardiac resynchronization therapy data aggregation engine of the system of FIG. 1.

FIG. 1 is a block diagram illustrating example system 10, which may be used in association with aggregating and reporting CRT performance data for an entire population of patients, e.g., all patients treated with CRT at a particular clinic. System 10 includes implantable medical devices (IMD) 12A-12N (collectively "IMDs 12" or "IMD 12"), network 14, data repository 16, and server 18. IMDs 12 are communicatively connected to data repository 16 and server 18 via network 14. IMDs 12 and server 18 are configured to periodically communicate with one another over network 14 to collect patient, therapy, and device data from IMDs 12 in data repository 16. System 10 may be implemented, in some aspects, with general network technology and functionality similar to that provided by the Medtronic CareLink® Network developed by Medtronic, Inc., of Minneapolis, Minn. As indicated in the block diagram of FIG. 2, in one example, CRT data aggregation engine 19 includes collection module 20, aggregation module 22, and reporting module 24, the structure and functions of which are described in detail below.

In some examples, IMDs 12 may not be connected directly to network 14 but, instead, may be configured to communicate wirelessly with an intermediate device located near the IMD and the patient within whom the IMD is implanted. For example, one or more of IMDs 12 may be implanted within patients that use a home patient monitoring system, which is configured to communicate via telemetry with the IMD. In such an example, IMD 12 may periodically transmit data from the device implanted within the patient to the external monitor, which, in turn, may transmit the data over network 14 to server 18 and data repository 16. In another example, the patient within whom one of IMDs 12 is implanted may periodically visit a clinic for an appointment with their physician. The physician or another clinician may employ an external programming device, which is configured to communicate with and configure IMD 12, to upload data from the IMD to the programmer. The physician programmer, in such an example, may then transmit the data over network 14 to server 18 and data repository 16.

Each of IMDs 12 may include an implantable pacemaker that provides electrical signals to and senses electrical signals generated by a patient's heart via electrodes coupled to one or more leads connected to the device. In addition to pacing therapy, IMD 12 may deliver other types of stimulation therapy, including, e.g., AV nodal stimulation and/or other forms of neurostimulation. In some examples, IMD 12 may also include cardioversion and/or defibrillation functionalities.

In one example, IMD 12 may be coupled to a number of leads, each of which may include a number of electrodes. IMD 12 may be implanted in a number of locations within a patient's body and the leads connected to the IMD may be tunneled intravenously from the implantation location to various locations near or within the heart of the patient. For example, IMD 12 may be implanted in a subcutaneous tissue pocket in the abdomen or within the chest cavity of the patient. IMD 12 may be employed in conjunction with one or more external devices with which the device is configured to communicate wirelessly, e.g., via various telemetry technologies. For example, IMD 12 may be employed in conjunction with an external physician programmer configured to send data to and receive data from the IMD and program operational parameters by which the IMD delivers therapy to the patient. Additionally, the patient within whom IMD 12 is implanted may use a patient monitoring device that periodically communicates with the IMD, e.g., to receive patient, therapy, and operational data from the device.

With regard to the therapeutic function of IMDs 12, each such device, in one example, may be connected to two leads that extend into the heart of a patient to sense electrical activity of and/or deliver electrical stimulation to the heart. In one example, a right ventricular (RV) lead extends from IMD 12 through one or more veins (not shown), the superior vena cava (not shown), and right atrium, and into the right ventricle of the patient's heart. The RV lead may be used to deliver RV pacing to the heart of the patient. IMD 12 may also be connected to a left ventricular (LV) lead that extends through one or more veins, the vena cava, the right atrium, and into the coronary sinus to a region adjacent to the free wall of the left ventricle of the heart. The LV lead may be used to deliver LV pacing to the heart.

In some examples, the LV lead may be used in combination with the RV lead to deliver biventricular pacing to the heart, which may provide cardiac resynchronization therapy (CRT) to the patient. CRT may be used to treat heart failure-inducted conduction disturbances and/or ventricular dyssynchrony. In some cases, CRT may help restore the mechanical sequence of ventricular activation and contraction. In some examples, CRT may involve biventricular pacing, e.g., via the RV lead and LV lead, to synchronize the contraction of both ventricles. In other examples, CRT may involve pacing one of the ventricles, e.g., the LV via the LV lead, to synchronize its contraction with that of the other ventricle.

In addition to the RV and LV leads, in some examples, IMD 12 may be connected to a right atrial (RA) lead. The RA lead may be arranged to extend from IMD 12 through one or more veins and the vena cava, and into the right atrium of the patient's heart. The RA lead may be positioned in the inferior portion of the right atrium. In some examples, the RA lead may be positioned in the posterior portion of the right atrium of the heart of the patient around the coronary sinus ostium, such as posteriorly to the coronary sinus ostium, and along the septum that separates the right and left atria. For example, the RA lead connected to IMD 12 may be positioned such that the lead may sense electrical activity within the right atrium, pace the right atrium, and also deliver a stimulation signal to or proximate to the AV node.

In another example, IMD 12 may be connected to an additional lead or lead segment that deploys one or more electrodes within the vena cava or other vein, or within or near the aorta. Additionally, in one example, IMD 12 may be connected to one or more additional intravenous or extravascular leads or lead segments that deploy one or more electrodes epicardially, e.g., near an epicardial fat pad, or proximate to the vagal nerve. In another example, IMD 12 need not be connected to one of the ventricular leads described above, such as where CRT is provided by pacing one ventricle, rather than both ventricles.

IMD 12 may sense electrical signals attendant to the depolarization and repolarization of the heart of the patient via electrodes coupled to at least one of the leads connected to the device, e.g., the LV or RV lead described above. In some examples, IMD 12 provides pacing pulses to the heart of the patient based on the electrical signals sensed within the heart. The configurations of electrodes used by IMD 12 for sensing and pacing may be unipolar or bipolar.

In one example, IMD 12 may trigger ventricular pacing, e.g., RV, LV, or biventricular pacing, based on atrial depolarizations sensed via the RA lead. As another example, the RA lead may deliver atrial pacing, and IMD 12 may trigger ventricular pacing based on atrial-paced events. In some examples, the RV and/or LV lead may sense ventricular depolarizations, and IMD 12 may trigger ventricular pacing, e.g., RV, LV, or biventricular pacing, based on whether the RV and/or LV lead detects an intrinsic ventricular depolarization within a defined time interval following the atrial sensed or paced event. The time interval between an atrial sensed or paced event and delivery of a pacing pulse to one or more of the ventricles may be referred to as an AV interval.

In some examples, IMD 12 may also provide neurostimulation therapy, defibrillation therapy and/or cardioversion therapy via electrodes located on one of the leads connected to the device. In any event, IMD 12 is configured to deliver CRT to the heart of the patient, either by pacing one or both of the left and right ventricles, and store CRT performance data, as well as data about the patient and operation of the device, e.g., stimulation parameters by which the CRT is delivered.

As noted above, in some examples, each of IMDs 12 may be employed in conjunction with one or more external electronic devices that are configured to communicate with the respective IMDs. For example, each of IMDs 12 may be employed in conjunction with one or both of an external programmer and patient monitor, both of which are configured to communicate with each respective IMD. The programmer may be a handheld computing device, desktop computing device, a networked computing device, or other electronic device. Similarly, the patient monitor may be a handheld computing device, desktop computing device, a networked computing device, or other electronic device. The patient monitor may be a device that reads data from IMD 12 and uploads the data to server 18 via network 14, e.g., automatically or in response to a command from a patient or other user. The programmer may also be configured to receive data from IMD 12 and upload the data to server 18 via network 14, e.g., at the behest of a clinician during a clinic visit by the patient within whom the IMD is implanted.

The programmer and patient monitor may, but typically will not, be co-located. Instead, the programmer and patient monitor may individually communicate with IMD 12 when co-located with the IMD at respective times. For example, the programmer may be used by a clinician in a clinical setting to communicate with IMD 12, as noted above, and the patient monitor may communicate with the IMD in a patient's home, automatically or in response to a user command.

Figure 3:
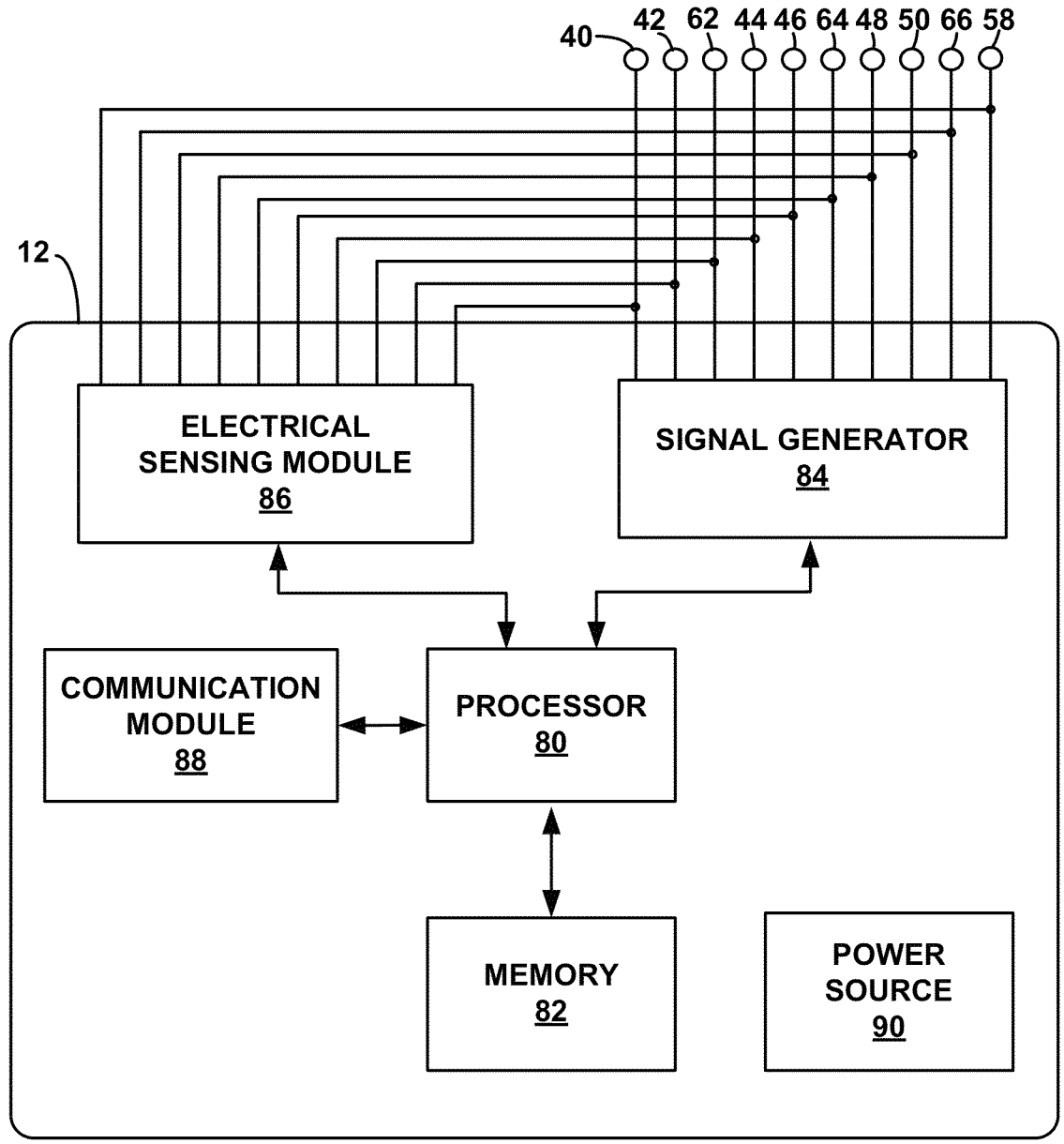
FIG. 3 is a block diagram illustrating an example implantable medical device that may be used in conjunction with the system of FIG. 1.

FIG. 3 is a functional block diagram illustrating an example configuration of an IMD 12. IMD 12 includes a processor 80, memory 82, a signal generator 84, an electrical sensing module 86, a sensor 87, a communication module 88, and a power source 90. Memory 82 may include computer-readable instructions that, when executed by processor 80, cause IMD 12 and processor 80 to perform various functions attributed to IMD 12 and processor 80 herein. Memory 82 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a microcontroller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more microcontrollers, one or more DSPs, one or more ASICs, or one or more FPGAs, as well as other discrete or integrated logic circuitry. The functions attributed to processor 80 herein may be embodied as software, firmware, hardware or any combination thereof.

Signal generator 84 is electrically coupled to electrodes 40, 42, 44, 46, 48, 50, 58, 62, 64, and 66, e.g., via conductors of the respective leads 18, 20, 22, or, in the case of housing electrode 58, via an electrical conductor disposed within housing 60 of IMD 12. Leads 18, 20, and 22 may, e.g., correspond to RV, LV, and RA leads described above. Signal generator 84 is configured to generate and deliver electrical stimulation therapy to heart 12. For example, signal generator 84 may deliver defibrillation pulses to heart 12 via at least two electrodes 58, 62, 64, 66. Signal generator 84 may deliver CRT pacing pulses via the ring electrodes 40, 44, 48 coupled to leads 18, 20, and 22, respectively, and/or the helical electrodes 42, 46, and 50 of leads 18, 20, and 22, respectively. In some implementations, signal generator 84 delivers pacing, cardioversion, or defibrillation stimulation in the form of electrical pulses. In other implementations, signal generator 84 may deliver one or more of these types of stimulation in the form of other signals, such as sine waves, square waves, or other substantially continuous time signals.

Processor 80 controls signal generator 84 to deliver stimulation therapy to the heart of a patient. Processor 80 may control signal generator 84 to deliver stimulation according to a selected one or more therapy programs, which may be stored in memory 82. For example, processor 80 may control signal generator 84 to deliver electrical pulses with amplitudes, pulse widths, frequencies, or electrode polarities specified by the selected one or more therapy programs.

Processor 80 may select which of electrodes 40, 42, 44, 46, 48, 50, 58, 62, 64, and 66 delivers electrical pulses. For example, signal generator 84 may include a switch module that processor 80 may use to select, e.g., via a data/address bus, which of the available electrodes are used to deliver CRT pacing, cardioversion, or defibrillation pulses. The switch module may include a switch array, switch matrix, multiplexer, or any other type of switching device suitable to selectively couple electrical pulses to electrodes selected by processor 80.

Electrical sensing module 86 monitors signals from at least one of electrodes 40, 42, 44, 46, 48, 50, 58, 62, 64 or 66 in order to monitor electrical activity of heart 12. Processor 80 may select which of electrodes 40, 42, 44, 46, 48, 50, 58, 62, 64, and 66 function as sense electrodes. For example, electrical sensing module 86 may include a switch module that processor 80 may use to select, e.g., via a data/address bus, which of the electrodes are used to monitor electrical activity of heart 12.

Electrical sensing module 86 may include multiple detection channels, each of which may comprise an amplifier. In response to the signals from processor 80, the switch module within the electrical sensing module 86 may couple selected electrodes to each of the detection channels.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 12 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

A portion of memory 82 may be configured as a plurality of recirculating buffers, capable of holding a series of measured intervals, which may be analyzed by processor 80 to determine whether the patient's heart 12 is presently exhibiting atrial or ventricular tachyarrhythmia, or other types of arrhythmias, e.g., premature ventricular contractions (PVCs). Processor 80 may detect tachyarrhythmia using any suitable tachyarrhythmia detection algorithm. In the event that processor 80 detects an atrial or ventricular tachyarrhythmia, data associated with such events may be stored in memory 82, e.g., for use in association with CRT performance data as described in this disclosure, and an anti-tachyarrhythmia pacing regimen may be loaded by processor 80 and implemented using signal generator 84.

Communication module 88 includes any suitable hardware, firmware, software or any combination thereof for communicating with another device, such as the above described external programmer and/or patient monitor. Under the control of processor 80, communication module 88 may receive downlink telemetry from and send uplink telemetry to the programmer and/or patient monitor with the aid of an antenna (not shown), which may be internal and/or external. Processor 80 may provide the data to be uplinked to the programmer 24 and/or patient monitor and the control signals for telemetry circuitry within communication module 88, e.g., via an address/data bus.

Processor 80 may transmit atrial and ventricular heart signals (e.g., EGMs) detected by atrial and ventricular sense amplifier circuits within electrical sensing module 86 to the programmer and/or patient monitor. Additionally, the programmer and/or patient monitor may interrogate IMD 12 to receive the EGMs. Processor 80 may provide stored and/or real-time EGMs to the programmer and/or patient monitor via communication module 88.

Processor 80 may store the EGMs in memory 82, and retrieve the stored EGMs from memory 82. Processor 80 may also generate marker channel data and store marker channel data in memory 82. Marker channel data may indicate the occurrence and timing of sensing, diagnosis, and therapy events, e.g., P-waves, R-waves, tachyarrhythmia (e.g., tachycardia or fibrillation), pacing pulses, anti-tachycardia pacing (ATP), cardioversion shocks, or defibrillation shocks, detected, diagnosed, or undertaken by IMD 12.

Processor 80 may store EGMs corresponding to physiological episodes, such as tachyarrhythmias or other types of cardiac rhythm events, in memory 82. For example, processor 80 may store EGMs for atrial and ventricular tachycardia and fibrillation episodes, in response to the detection of the tachycardia or fibrillation.

The marker channel data and EGMs may be correlated to CRT performance data for IMD 12 and employed in examples according to this disclosure when a number of sets of such data are aggregated for a number of patients and associated IMDs.

The various components of IMD 12 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Regardless of the particular configuration of IMDs 12 or whether IMDs 12 are configured to communicate directly with network 14 or via one or more external devices like a programmer or patient monitor, periodically data is transmitted from each of the IMDs over network 14 to server 18 and data repository 16. For example, IMDs 12 may track and store data related to CRT delivery to the patients within whom the devices are implanted, as well as data about the patients and the operation of the devices.

In one example, each of IMDs 12 is configured to store CRT performance data, including, e.g., a percentage of CRT delivery and a percentage loss of CRT delivery by the respective IMD to the respective patient. The percentage of CRT delivery and associated percentage loss of CRT delivery may be equivalent to the amount of time therapy is delivered or not delivered to the patient represented as a percentage of a total time over which IMD 12 was intended to be delivering CRT.

The sum of the percentage of CRT delivery and the percentage loss of CRT delivery equals approximately 100%.

Additionally, IMD 12 may be configured to store data related to cardiac rhythm events sensed by the electrodes connected to the leads coupled to the IMD. For example, IMD 12 may store incidences of certain types of arrhythmias detected for the patient, including, e.g., AT/AF and/or PVCs. IMD 12 may also store other information that may be related to CRT performance, including, e.g., data related to the patient within whom the device is implanted and parameters, e.g., stimulation parameters that define CRT delivered to the patient, e.g., according to one or more CRT programs stored on the device. Any or all of the CRT performance, cardiac rhythm event, patient, and device operational data may be transmitted periodically from IMDs 12 over network 14 to server 18 and data repository 16.

Network 14 may include one or more terrestrial and/or satellite networks interconnected to provide a means of communicatively connecting IMDs 12 to data repository 16 and server 18. For example, network 14 may be a private or public local area network (LAN) or Wide Area Network (WANs). Network 14 may include both wired and wireless communications according to one or more standards and/or via one or more transport mediums. For example, network 14 may include wireless communications according to one of the 802.11 or Bluetooth specification sets, or another standard or proprietary wireless communication protocol. Network 14 may also include communications over a terrestrial cellular network, including, e.g., a GSM (Global System for Mobile Communications), CDMA (Code Division Multiple Access), EDGE (Enhanced Data for Global Evolution) network. Data transmitted over network 14, e.g., from IMDs 12 to data repository 16 may be formatted in accordance with a variety of different communications protocols. For example, all or a portion of network 14 may be a packet-based, Internet Protocol (IP) network that communicates data from IMDs 12 to data repository 16 in Transmission Control Protocol/Internet Protocol (TCP/IP) packets, over, e.g., Category 5, Ethernet cables.

Data repository 16 may include, e.g., a standard or proprietary database or other data storage and retrieval mechanism. Data repository 16 may be implemented in software, hardware, and combinations of both. For example, data repository 16 may include proprietary database software stored on one of a variety of storage mediums on a data storage server connected to network 14 and configured to collect battery life data from IMDs. Storage medium included in or employed in cooperation with data repository 16 may include, e.g., any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Server 18 includes CRT data aggregation engine 19, which may be employed, as described below, to aggregate and report CRT performance data collected from IMDs 12 and correlated to one or more cardiac rhythm events of the respective patients within whom the IMDs are implanted. Server 18 may be any of several different types of network devices. For example, server 18 may include a data processing appliance, web server, specialized media server, personal computer operating in a peer-to-peer fashion, or another type of network device. Additionally, although example system 10 of FIG. 1 includes one server 18, other examples may include a number of collocated or distributed servers configured to aggregate and report CRT performance data collected from IMDs 12 and stored in data repository 16 individually or in cooperation with one another.

Although data repository 16 and server 18 are illustrated as separate components in example system 10 of FIG. 1, in other examples the two components may be combined or may each be distributed amongst more than one device. For example, server 18 may store data repository 16 and control the repository to periodically store CRT performance data collected from IMDs 12. In another example, data repository 16 may be distributed among a number of separate devices, e.g., a number of database servers, and server 18 may include a number of co-located or distributed servers configured to operate individually and/or in cooperation with one another and with the various devices comprising data repository 16.

Regardless of the particular configuration of system 10, or other example systems according to this disclosure, the system may be employed to collect CRT performance data correlated to cardiac rhythm event data for each of the patients within whom IMDs 12 are implanted, aggregate the CRT performance data correlated to the cardiac rhythm event data for a particular population of the patients, e.g., patients treated at the same clinic, and generate a report including the aggregation of the CRT performance data correlated to the cardiac rhythm event data for the target population.

For example, CRT data aggregation engine 19 executed on server 18 may collect CRT performance data for correlated to cardiac rhythm event data for the patients within whom IMDs 12 are implanted, aggregate the CRT performance data correlated to the cardiac rhythm event data for a target population of the patients, and generate a report including the aggregation of the CRT performance data correlated to the cardiac rhythm event data for the target population. As noted above, an example configuration of data aggregation engine 19 including collection module 20, aggregation module 22, and reporting module 24 is illustrated in the block diagram of FIG. 2.

In one example, collection module 20 of aggregation engine 19 may collect CRT performance data correlated to one or more different types of cardiac rhythm events including, e.g., AT/AF, PVC, or a ventricular sensing episode (VSE). A VSE may correspond to any occurrence of a consecutive sequence of ventricular depolarization events that occur in the heart of a patient and which are sensed by IMD 12. A VSE may occur due to, e.g., ventricular tachyarrhythmia, supraventricular tachyarrhythmia, conducted atrial tachyarrhythmia, an intrinsic rate above the programmed upper tracking rate, or any reason that may cause or allow ventricular depolarizations to occur before expiration of a programmed escape interval. In one example, the CRT performance data correlated to AT/AF, PVC, and/or various types of VSEs may be collected by collection module 20 of aggregation engine 19, e.g., from data repository 16 storing CRT performance and related data collected from IMDs 12.

The data in data repository 16 including CRT performance and related data collected from IMDs 12 may have previously been processed to correlate the CRT data to other relevant data, e.g., possible causes for CRT loss such as AT/AF, PVC, and/or various types of VSEs. For example, data may be received from IMDs 12 over network 14, either directly or indirectly via a programmer or patient monitor or other such device, as described above. The separate types of data, e.g., CRT performance data, patient data, cardiac rhythm event data, and device data, may be correlated by an algorithm configured to automatically, or in conjunction with user interaction, draw connections between CRT performance for the IMDs and other data. For example, an algorithm may be configured to correlate the loss of CRT delivery by IMDs 12 to one or more reasons that may have caused the IMDs to not continue delivering CRT to the patients within whom the IMDs are implanted, including, e.g., one or more of AT/AF, PVC, or various types of VSEs. Example techniques for determining possible causes of loss of CRT delivery and also classifying certain types of causes, e.g., classifying different types of VSEs that may have caused the loss of CRT, are described in U.S. application Ser. No. 13/297,104, filed Nov. 15, 2011, and entitled "CARDIAC RESYNCHRONIZATION THERAPY LOSS DIAGNOSTICS," the entire content of which is incorporated herein by this reference.

Regardless of how the CRT data is correlated to other related data, aggregation module 22 of CRT data aggregation engine 19 may, in one example, aggregate the CRT performance data correlated to, e.g., AT/AF, PVC, and/or various types of VSEs for a particular target population of patients. For example, aggregation module 22 of CRT data aggregation engine 19 may aggregate the CRT performance data correlated to AT/AF, PVC, and/or various types of VSEs for all of the patients that are treated at a particular clinic or by a particular physician.

Aggregation module 22 of CRT data aggregation engine 19 may be configured to aggregate CRT performance data correlated to cardiac rhythm and other related data in a variety of ways. In one example, aggregation module 22 aggregates CRT performance data, e.g., percentage of CRT delivery and/or percentage loss of CRT delivery, correlated to patient data for the patients within whom the IMDs are implanted, the percentage of CRT delivery during AT/AF experienced by the patients, the percentage of the loss of CRT delivery that is due to one or more of AT/AF, a PVC, a VSE, or other types of cardiac rhythm events, or the set of CRT delivery parameters for each of the IMDs. Other reasons for CRT loss aside from AT/AF, PVCs, VSEs include, as examples, NSTs, premature atrial contractions that are too fast for IMD 12 to track according to a programmed detection criterion, premature ventricular contractions that are too slow for IMD 12 to identify according to a programmed detection criterion, treated VSEs, or atrial undersensing. In one example, aggregation module 22 aggregates a particular population of patients within whom some of IMDs 12 are implanted by the percentage of CRT delivery by the respective IMD to the respective patient. For example, aggregation module 22 may aggregate patients in a population into different percentage levels of CRT delivery. In one example, aggregation module 22 aggregates patients in the target population, e.g., all the patients at a particular clinic receiving CRT from associated IMDs 12, into a first group of patients receiving less than 90% CRT delivery, a second group of patients receiving between 90% to 95% CRT delivery, and a third group of patients receiving greater than 95% CRT delivery. These and other examples of aggregating CRT performance data correlated to various types of related data are described in detail with reference to FIGS. 4-8.

Reporting module 24 of aggregation engine 19 executed on server 18 is configured to generate a report that includes, in one example, the aggregated CRT performance data correlated to AT/AF, PVC, and/or VSEs for all of the patients in the target population. Organizations and individual clinicians may view and analyze the report, e.g., to discern the percentage loss of CRT delivery for the patients, and the extent to which different causes contributed to the loss of CRT delivery. In one example, reporting module 24 generates a report that indicates the percentage of loss of CRT delivery and a percentage contribution of each of AT/AF, PVC, and/or VSE to the total loss of CRT for the target population for which the CRT and associated data was aggregated by aggregation module 22. For example, the report generated by reporting module 24 of aggregation engine 19 indicates for one patient that of the total time over which CRT therapy was intended to be delivered there was actually 88.8% CRT delivery. For the same patient, the report also indicates that of the 21.2% loss of CRT delivery, 14% was correlated to AT/AF, 72% was correlated to PVC, and 14% was correlated to other types of cardiac rhythm events, including, e.g., various types of VSEs.

In another example, reporting module 24 of CRT data aggregation engine 19 generates a report including an aggregation of patients by the percentage of CRT delivery by a respective IMD 12 to the respective patient, an aggregation of patients by the percentage of CRT delivery during AT/AF for all of the patients that experienced AT/AF, and/or an aggregation of patients by the percentage of the loss of CRT delivery that is due to one or more of AT/AF, a PVC, a VSE, or other types of cardiac rhythm events. For example, reporting module 24 may generate a report including a histogram that aggregates patients in a target population, e.g., all the patients at a particular clinic receiving CRT from associated IMDs 12, into a first group of patients receiving less than 90% CRT delivery, a second group of patients receiving between 90% to 95% CRT delivery, and a third group of patients receiving greater than 95% CRT delivery.

Although the foregoing examples have been described with reference to CRT data aggregation engine 19 including collection module 20, aggregation module 22, and reporting module 24, in other examples such processing engines or other mechanisms may be physically and/or logically differently arranged. For example, CRT data aggregation engine 19 may include a collection module and an aggregation module, in which the aggregation module aggregates CRT performance data and generates reports of the aggregated data. A wide variety of other logical and physical arrangements are possible in order to implement the functionality attributed to the example of server 18 including CRT data aggregation engine 19 illustrated in FIGS. 1 and 2. Additionally, CRT data aggregation engine 19 may be embodied as software, firmware, hardware or any combination thereof.

Figure 4:
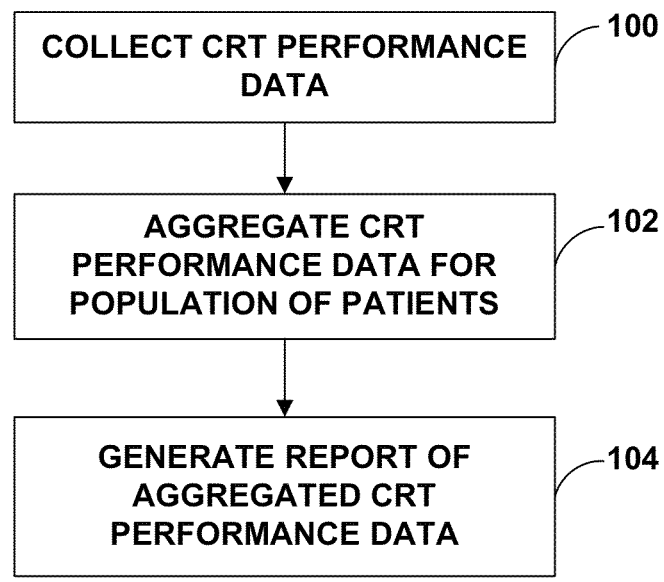
FIG. 4 is a flowchart illustrating an example method of aggregating cardiac resynchronization therapy data for a number of patients.

FIG. 4 is a flowchart illustrating an example method of aggregating and reporting CRT performance data for a target population of patients within whom an IMD that delivers the CRT is implanted. The example method of FIG. 4 includes collecting cardiac resynchronization therapy (CRT) performance data correlated to cardiac rhythm event data for a plurality of patients in which an implantable medical device (IMD) configured to deliver CRT is implanted (100), aggregating, with a computing device, the CRT performance data correlated to the cardiac rhythm event data for a target population of patients within the plurality of patients (102), and generating, with the computing device, a report comprising the aggregation of the CRT performance data correlated to the cardiac rhythm event data for the population of patients (104).

The example method of FIG. 4 is described as executed by various components of system 10 of FIG. 1 and, in many cases, by CRT data aggregation engine 19 implemented on server 18. However, the techniques described with reference to the method of FIG. 4 may be practiced in conjunction with other systems including different configurations than system 10.

In one example, CRT data aggregation engine 19 executed on server 18 may collect CRT performance data correlated to cardiac rhythm event data for a number of patients within whom IMDs 12 are implanted. In particular, collection module 20 of aggregation engine 19 may collect CRT performance data correlated to one or more different types of cardiac rhythm events. Example cardiac rhythm events include AT/AF, PVC, or a ventricular sensing episode (VSE) for a number of patients, e.g., a number of patients receiving treatment at a number of locations across a wide geographic area, such as across the United States of America. In one example, the CRT performance data correlated to AT/AF, PVC, and/or various types of VSEs may be collected by collection module 20 of aggregation engine 19, e.g., from data repository 16 storing CRT performance and related data collected from IMDs 12.

The data in data repository 16 including CRT performance and related data collected from IMDs 12 may have previously been processed to correlate the CRT data to other relevant data, e.g., possible causes for CRT loss such as AT/AF, PVC, and/or various types of VSEs. For example, data may be received from IMDs 12 over network 14, either directly or indirectly via a programmer or patient monitor or other such device, as described above. As noted above, this may be accomplished by means of IMDs 12 or a local electronic device such as a programmer or patient monitor communicating data over network 14 to server 18 and data repository 16, which process, in one example, may be similar in configuration and function to the Medtronic CareLink® Network developed by Medtronic, Inc., of Minneapolis, Minn. The separate types of data, e.g., CRT performance data, patient data, cardiac rhythm event data, and device data, may be correlated by an algorithm configured to automatically or in conjunction with user interaction draw connections between CRT performance for the IMDs and other data. For example, an algorithm may be configured to correlate the loss of CRT delivery by IMDs 12 to one or more reasons that may have caused the IMDs to not continue delivering CRT to the patients within whom the IMDs are implanted, including, e.g., one or more of AT/AF, PVC, or various types of VSEs. Example techniques for determining possible causes of loss of CRT delivery and also classifying certain types of causes, e.g., classifying different types of VSEs that may have caused the loss of CRT, are described in U.S. application Ser. No. 13/297,104, filed Nov. 15, 2011, and entitled "CARDIAC RESYNCHRONIZATION THERAPY LOSS DIAGNOSTICS," the entire content of which is incorporated herein by this reference.

Regardless of how the CRT data is correlated to other related data, aggregation module 22 of CRT data aggregation engine 19 may, in one example, aggregate the CRT performance data correlated to, e.g., AT/AF, PVC, and/or various types of VSEs for a particular target population of patients. For example, aggregation module 22 of CRT data aggregation engine 19 may aggregate the CRT performance data correlated to AT/AF, PVC, and/or various types of VSEs for all of the patients that are treated at a particular clinic or by a particular physician. In this manner, aggregation module 22 of CRT data aggregation engine 19 is configured to process the collected CRT performance data collected by collection module 20 to prepare the data for reporting, including, putting together a set of data for a particular population of patients within the population collected by collection module 20, e.g., patients treated by the same clinic or physician, and relating or arranging the data in a particular manner for reporting.

Aggregation module 22 of CRT data aggregation engine 19 may be configured to aggregate CRT performance data correlated to cardiac rhythm and other related data in a variety of ways. In one example, aggregation module 22 aggregates CRT performance data, e.g., percentage of CRT delivery and/or percentage loss of CRT delivery, correlated to patient data for the patients within whom the IMDs are implanted, the percentage of CRT delivery during AT/AF experienced by the patients, the percentage of the loss of CRT delivery that is due to one or more of AT/AF, a PVC, a VSE, or other types of cardiac rhythm events, or the set of CRT delivery parameters for each of the IMDs. In one example, aggregation module 22 aggregates the patient data for each patient treated at a particular clinic, e.g., correlated to the percentage of the loss of CRT delivery that is due to each of AT/AF, a PVC, a VSE, and other types of cardiac rhythm events, and the set of CRT delivery parameters for each of the IMDs implanted within each patient in the second group of patients. In this example, one or more patients treated at the clinic may have experienced a loss of CRT delivery over a period of time over which data was collected for the patient, e.g., between clinic visits or over a certain number of days, weeks, months, etc. The loss of CRT delivery may be correlated to several different possible causes, e.g., using the techniques, described in U.S. application Ser. No. 13/297,104, filed Nov. 15, 2011, and entitled "CARDIAC RESYNCHRONIZATION THERAPY LOSS DIAGNOSTICS," The correlation between loss of CRT delivery and causes thereof may attribute different causes to the loss of CRT delivery on a percentage basis to express the degree to which each possible cause contributed to the loss of CRT. In addition to CRT loss causes, the patient data may be aggregated with the stimulation parameters according to which CRT was programmed to be delivered. Thus, in one example, data for each patient may be aggregated with the degree to which each of AT/AF, a PVC, a VSE, and other types of cardiac rhythm events contributed to the total CRT loss experienced by the patient and the stimulation parameters according to which CRT was programmed to be delivered the respective IMD 12 implanted within the patient.

In another example, aggregation module 22 aggregates a particular population of patients within whom some of IMDs 12 are implanted by the percentage of CRT delivery by the respective IMD to the respective patient. For example, aggregation module 22 may aggregate patients treated at a particular clinic into different percentage levels of CRT delivery. In one example, aggregation module 22 aggregates patients in the target population, e.g., all the patients at a particular clinic receiving CRT from associated IMDs 12, into a first group of patients receiving less than 90% CRT delivery, a second group of patients receiving between 90% to 95% CRT delivery, and a third group of patients receiving greater than 95% CRT delivery.

In another example, aggregation module 22 aggregates a particular population of patients within whom some of IMDs 12 are implanted by the percentage of CRT delivery during AT/AF for all of the patients that experienced AT/AF. For example, aggregation module 22 may aggregate patients treated at a particular clinic, which experienced CRT delivery loss and some period of AT/AF, by the amount of CRT was delivered to the patient during the AT/AF episode(s). In one example, aggregation module 22 aggregates patients in the target population experiencing some period of AT/AF into a first group of patients receiving less than 90% CRT delivery during AT/AF, a second group of patients receiving between 90% to 95% CRT delivery during AT/AF, and a third group of patients receiving greater than 95% CRT delivery during AT/AF.

In one example, aggregation module 22 further groups the patients treated at the clinic and experiencing AT/AF by the duration of the AT/AF episode(s). For example, aggregation module 22 may aggregate the patients with paroxysmal AT/AF episodes (e.g., 6 hours to 7 days of AT/AF) into a first group of patients receiving less than 90% CRT delivery during AT/AF, a second group of patients receiving between 90% to 95% CRT delivery during AT/AF, and a third group of patients receiving greater than 95% CRT delivery during AT/AF, and separately aggregate the patients with persistent AT/AF episodes (e.g., more than 7 days of AT/AF) into a first group of patients receiving less than 90% CRT delivery during AT/AF, a second group of patients receiving between 90% to 95% CRT delivery during AT/AF, and a third group of patients receiving greater than 95% CRT delivery during AT/AF.

In one example, aggregation module 22 aggregates a particular population of patients within whom some of IMDs 12 are implanted by the percentage of the loss of CRT delivery that is due to one or more different possible causes, e.g., one or more of AT/AF, a PVC, a VSE, or other types of cardiac rhythm events. For example, aggregation module 22 may aggregate patients treated at a particular clinic, which experienced CRT delivery loss by the degree to which the CRT loss was caused by one or more different events, e.g., one or more of AT/AF, a PVC, a VSE, or other types of cardiac rhythm events. In one example, aggregation module 22 aggregates patients treated at a particular clinic by the primary reason the patients experienced loss of CRT delivery. For example, the data for patients at the clinic experiencing CRT loss may correlated to three possible causes for the loss of CRT, including, e.g., AT/AF, PVC, or another type of cardiac rhythm event including various types of VSEs. Of the three possible causes for CRT loss, aggregation module may group the patients by the cause with the highest percentage contribution to the CRT loss. Thus, for a patient for whom CRT loss was 14% caused by AT/AF, 72% caused by PVC, and 14% caused by other reasons, aggregation engine 22 would aggregate this patient with other patients for whom the primary cause of CRT loss was PVCs. In one such an example, aggregation engine 22 may aggregate patients by the primary cause for the loss of CRT delivery, including, e.g., into a first group of patients for whom the primary reason for loss of CRT delivery was AT/AF, a second group of patients for whom the primary reason for loss of CRT delivery was PVC, and a third group of patients for whom the primary reason for loss of CRT delivery was another type of cardiac rhythm event including various types of VSEs.

Aggregation module 22 of CRT data aggregation engine 19 may be configured to correlate CRT performance data and/or other data, e.g. cardiac rhythm data to other types of data. As mentioned above, aggregation module 22 may be configured to correlate CRT performance and/or the occurrence and duration of AT/AF to different outcomes, including, e.g., mortality, hospitalizations, and quality of life metrics.

Reporting module 24 of aggregation engine 19 executed on server 18 is configured to generate a report that includes, in one example, the aggregated CRT performance data correlated to AT/AF, PVC, and/or VSEs for all of the patients in the target population. Organizations and individual clinicians may view and analyze the report, e.g., to discern the percentage loss of CRT delivery for the patients, and the extent to which different causes contributed to the loss of CRT delivery. The content and arrangement of some example reports that may be generated by reporting module 24 of CRT data aggregation engine 19 are described with reference to FIGS. 5-8. However, the manner in which reporting module 24 generates such reports and how the reports are communicated to interested parties is first described.

Reporting module 24 of CRT data aggregation engine 19 is configured to generate electronic reports of the data aggregated by aggregation module 22. Reporting module 24 may generate reports in a variety of formats, including, e.g., Hypertext Mark-up Language (HTML), Extensible Mark-up Language (XML), Adobe's portable document format (PDF), word processing document formats, spreadsheet formats including comma and tab-separated formats, and the like. Reporting module 24 may be configured to generate reports with varying levels of interactivity. For example, reporting module 24 may be configured to generate a static electronic report that includes textual and graphical information representing the aggregation of the CRT performance data, which may be transmitted and viewed in electronic form but which does not include features for users interacting with the data in the report. In another example, reporting module 24 is configured to generate an interactive electronic report that includes textual and graphical information representing the aggregation of the CRT performance data, which users interact with, e.g., by clicking hyperlinked elements to navigate between various parts of the report or by filtering the number of patients included in each page of a report.

Reports generated by reporting module 24 may be communicated to users, e.g., organizations or individual clinicians, in a number of ways. In one example, electronic reports generated by reporting module 24 may be transmitted electronically to users, e.g., by electronic mail (e-mail), or by publishing such reports on a private or public network to make the reports available for downloading onto a remote computing device. In another example, electronic reports generated by reporting module 24 may be output, e.g., printed and mailed by ground or air mail, or otherwise physically delivered, to a clinic or an individual clinician.

Figure 8:
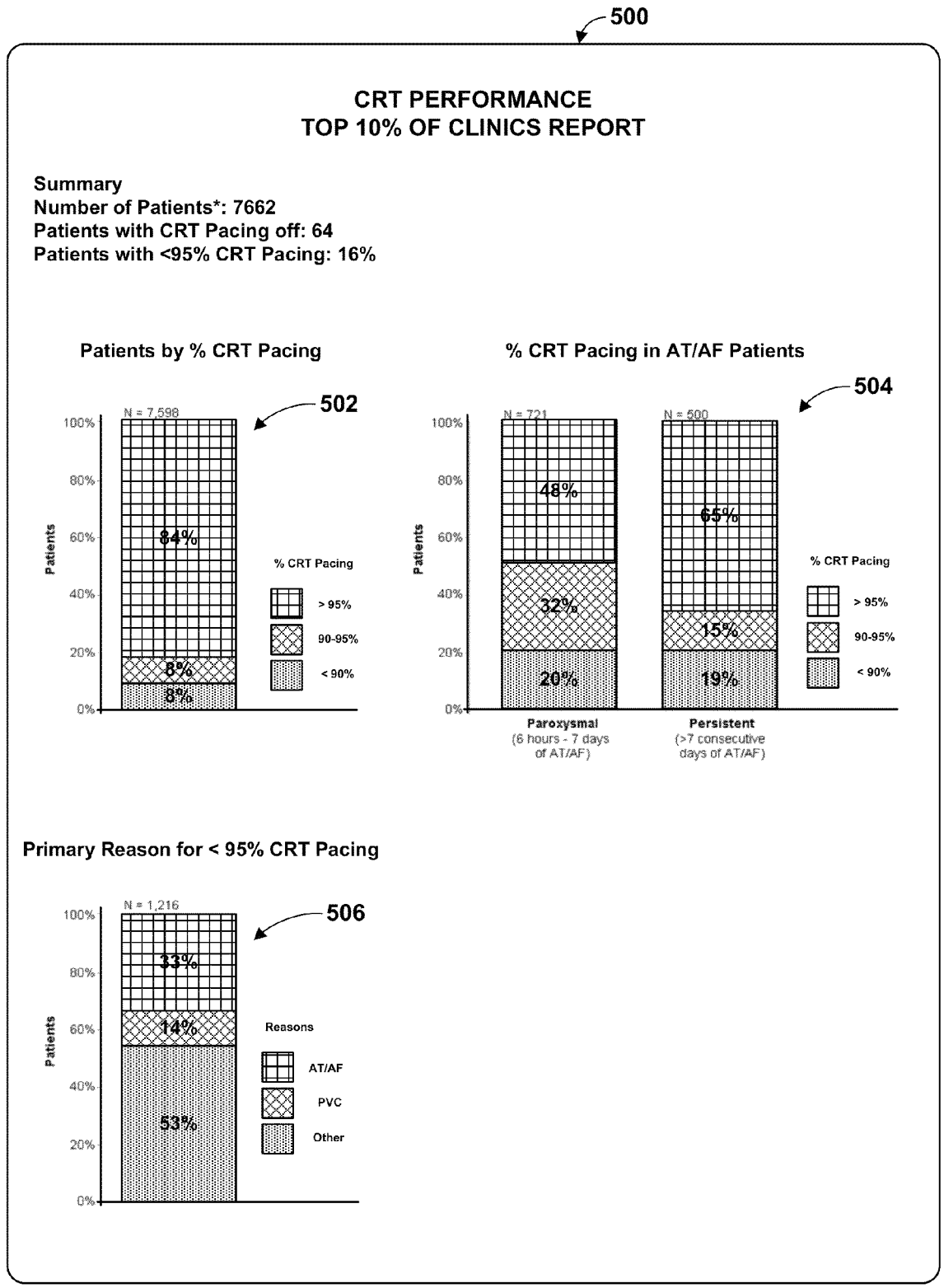

FIGS. 5-8 are example reports generated by reporting module 24, or another similar component of a system in accordance with this disclosure. FIGS. 5 and 6 are textual reports of CRT performance data for a group of patients treated at a particular clinic. FIGS. 7 and 8 are textual and graphical reports of CRT performance data for a group of patients. FIG. 7 is a report of CRT performance data for the patients treated at the clinic. FIG. 8 is a report of CRT performance data for patients treated at a number of high performing clinics, in particular, at clinics with CRT performance results in the top 10% of all of the clinics sampled.

FIG. 5 illustrates example report 200 generated by reporting module 24 of CRT performance data aggregated by aggregation module 22 for a number of patients treated at a particular clinic. Although report 200 of FIG. 5 lists 18 patients, in one example, this may be one of several pages including such data for a larger number of patients treated at the clinic. Report 200 includes patient data 202 and CRT performance data 204 correlated to a number of different other parameters, which is referred to in the report as "Clinical Data." In particular, report 200 includes patient data 202 including patient name, device information for the IMDs implanted within the patients, including device serial number and brand. Patient data 202 also includes the number of days between data reporting and the date data was transmitted from the respective IMD 12 over network 14 to server 18 and data repository 16. CRT performance data 204 includes the percentage of CRT delivery for each patient correlated to the percentage of time during the session period the patient was in AT/AF and the percentage of CRT delivery during AT/AF.

FIG. 6 includes another textual report generated by reporting module 24. In particular, FIG. 6 illustrates example report 300 generated by reporting module 24 of CRT performance data aggregated by aggregation module 22 for patients treated at the clinic. Report 300 includes patient data 302, CRT performance data 304, and programming data 304. In example report 300, patient data 302 includes patient name and the serial number of the IMD implanted within the patient. Report 300 also includes CRT performance data 304 which includes a number of possible reasons the patients at the clinic may have experienced a loss of CRT delivery. In particular, CRT performance data includes three possible reasons for loss of CRT delivery, including AT/AF, PVCs, and other types of cardiac rhythm events, which may include, e.g., various types of VSEs. Examples of VSEs include ventricular tachyarrhythmia, supraventricular tachyarrhythmia, conducted atrial tachyarrhythmia, an intrinsic rate above the programmed upper tracking rate, or any reason that may cause or allow ventricular depolarizations to occur before expiration of a programmed escape interval. The reasons for loss of CRT delivery indicate on a percentage of total loss of CRT basis the degree to which the loss of therapy delivery was caused by the particular event or episode, e.g., the percentage of total CRT loss that was caused by PVCs or by one or more AT/AF episodes. Patient data 302 and CRT performance data 304 is also correlated in report 300 to programming data 306, which includes a number of different parameters by which the respective IMDs implanted in the respective patients are configured to delivery CRT. Programming data 306 includes pacing modes for the CRT, sensed and programmed AV interval times, upper and lower tracking rates (in beats per minute), and a number of other CRT programming features, including conducted AT/AF response, atrial tracking recovery, and ventricular sense response (V. sense response).

As noted above, FIGS. 7 and 8 are textual and graphical reports of CRT performance data for a group of patients. FIG. 7 illustrates example report 400 generated by reporting module 24 of CRT performance data aggregated by aggregation module 22 for a number of patients treated at a particular clinic. Report 400 includes three histograms representing three different aggregations of CRT performance data correlated to cardiac rhythm event data for the patients at the clinic. Report 400 includes histogram 402, which illustrates patients aggregated by aggregation module 22 by the percentage of CRT delivery. In particular, histogram 402 of report 400 illustrates patients treated at the clinic with CRT aggregated into a first group of patients receiving less than 90% CRT delivery, a second group of patients receiving between 90% to 95% CRT delivery, and a third group of patients receiving greater than 95% CRT delivery. In the example of FIG. 7, 13% of patients at the clinic received less than 90% CRT delivery, 9% of patients received between 90% to 95% CRT delivery, and 78% of patients received greater than 95% CRT delivery.

Report 400 also includes histogram 404, which illustrates patients experiencing AT/AF aggregated by aggregation module 22 both by the length of time the AT/AF lasted and by the percentage of CRT delivery during AT/AF. Histogram 404 of report 400 aggregates patients treated at the clinic experiencing paroxysmal AT/AF episodes (e.g., 6 hours to 7 days of AT/AF) into a first group of patients receiving less than 90% CRT delivery during AT/AF, a second group of patients receiving between 90% to 95% CRT delivery during AT/AF, and a third group of patients receiving greater than 95% CRT delivery during AT/AF. Histogram 404 also separately aggregates the patients with persistent AT/AF episodes (e.g., more than 7 days of AT/AF) into a first group of patients receiving less than 90% CRT delivery during AT/AF, a second group of patients receiving between 90% to 95% CRT delivery during AT/AF, and a third group of patients receiving greater than 95% CRT delivery during AT/AF. In the example of FIG. 7, of the patients experiencing paroxysmal AT/AF episodes, 36% of patients at the clinic received less than 90% CRT delivery, 41% of patients received between 90% to 95% CRT delivery, and 23% of patients received greater than 95% CRT delivery. Additionally, of the patients experiencing persistent AT/AF episodes, 41% of patients at the clinic received less than 90% CRT delivery, 45% of patients received between 90% to 95% CRT delivery, and 14% of patients received greater than 95% CRT delivery.

Example report 400 also includes histogram 406, which illustrates a percentage breakdown of the primary reason for CRT loss for three different reasons, including AT/AF, PVC, and all other cardiac rhythm events. Histogram 406 presents an aggregation of the reasons for CRT loss only for patients that received less than 95% CRT delivery. Histogram 406 presents patients that received less than 95% of CRT delivery aggregated into three groups corresponding to three different primary reasons for CRT loss. In particular, histogram 406 presents an aggregation of the patients into a first group of patients for whom the primary reason for loss of CRT delivery was AT/AF, a second group of patients for whom the primary reason for loss of CRT delivery was PVC, and a third group of patients for whom the primary reason for loss of CRT delivery was another type of cardiac rhythm event including various types of VSEs. In the example of FIG. 7, 41% of patients lost CRT primarily because of AT/AF, 15% of patients lost CRT primarily because of PVC, and 44% of patients lost CRT primarily because of another type of cardiac rhythm event including various types of VSEs.

Example report 400 also includes programming data 408. Programming data 408 indicates on a percentage basis for all of the patients treated with CRT at the clinic which of three different programming features were activated for the CRT. In particular, programming data 408 indicates the percentage of patients with atrial tracking recovery, conducted AT/AF response, and ventricular sense response on. In the example of FIG. 7, 48% of all the patients received CRT with atrial tracking recovery on, 61% of all the patients received CRT with conducted AT/AF response on, and 76% of all the patients received CRT with ventricular sense response on.

FIG. 8 includes example report 500 of CRT performance data for patients treated at a number of high performing clinics, in particular, at clinics with CRT performance results in the top 10% of all of the clinics sampled. Report 500 includes histograms 502, 504, and 506, which are the same as histograms 402, 404, and 406, respectively, of report 400 of FIG. 7, except report 500 represents data for patients treated at the top 10% performing clinics for CRT therapy delivery. Reporting module 24 may generate report 400 and report 500, or another similar report representing data from patients treated at a number of locations, to enable interested parties to compare results at a particular clinic, or, in another example, by a particular clinician, to national averages or to a number of high performing clinics.

In one example, reporting module 24 generates a report that indicates the percentage of loss of CRT delivery and a percentage contribution of each of AT/AF, PVC, and/or VSE to the total loss of CRT for the target population for which the CRT and associated data was aggregated by aggregation module 22. For example, the report generated by reporting module 24 of aggregation engine 19 indicates for one patient that of the total time over which CRT therapy was intended to be delivered there was actually 88.8% CRT delivery. For the same patient, the report also indicates that of the 21.2% loss of CRT delivery, 14% was correlated to AT/AF, 72% was correlated to PVC, and 14% was correlated to other types of cardiac rhythm events, including, e.g., various types of VSEs.

In another example, reporting module 24 of CRT data aggregation engine 19 generates a report including an aggregation of patients by the percentage of CRT delivery by a respective IMD 12 to the respective patient, an aggregation of patients by the percentage of CRT delivery during AT/AF for all of the patients that experienced AT/AF, and/or an aggregation of patients by the percentage of the loss of CRT delivery that is due to one or more of AT/AF, a PVC, a VSE, or other types of cardiac rhythm events. For example, reporting module 24 may generate a report including a histogram that aggregates patients in a target population, e.g., all the patients at a particular clinic receiving CRT from associated IMDs 12, into a first group of patients receiving less than 90% CRT delivery, a second group of patients receiving between 90% to 95% CRT delivery, and a third group of patients receiving greater than 95% CRT delivery.

In addition to the foregoing data related to CRT performance, reporting module 24 may be configured to present additional data correlated to CRT performance data and/or other data, e.g. cardiac rhythm data. In one example, reporting module 24 is configured to generate a report including CRT performance and/or the occurrence and duration of AT/AF correlated to different patient outcomes, including, e.g., mortality, hospitalizations, and quality of life metrics. Additionally, reporting module 24 may present programmed and/or sensed ventricular rates during the occurrence of AT/AF to assist clinician management of rate control.

CRT performance data aggregation and reporting according to this disclosure may provide a number of advantages to organizations and individuals treating patients with CRT. CRT performance data aggregation and reporting according to this disclosure may provide an efficient mechanism by which an organization or individual may judge the quality of CRT provided to an entire population of patients. Additionally, the techniques described herein may allow interested parties to analyze the aggregated CRT performance data for trends regarding or causes of loss of CRT delivery and thereby formulate strategies for improving performance in the future. Organizations and individuals may also drill down from aggregated CRT performance data for an entire population of patients to a particular subset of patients. For example, organizations and individuals may drill down from aggregated CRT performance data for an entire population of patients to a subset of patients with below a threshold level of acceptable CRT performance, e.g., below a threshold level of percentage of CRT delivery or above a threshold level of loss of CRT delivery. By quickly and efficiently identifying the subset of patients with below a threshold level of acceptable CRT performance in this manner, interested parties may use the aggregated CRT performance data as an efficient triage tool for effectively responding to potentially harmful loss of treatment for certain patients.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components. The term "processor" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   collecting cardiac resynchronization therapy (CRT) performance data correlated to cardiac rhythm event data for a first group of patients in which an implantable medical device (IMD) configured to deliver CRT is implanted;
   aggregating, with a computing device, the CRT performance data correlated to the cardiac rhythm event data for a second group of patients from among the first group of patients; and
   generating, with the computing device, a report comprising the aggregation of the CRT performance data correlated to the cardiac rhythm event data for the second group of patients, wherein the CRT performance data for each patient in the first group of patients comprises a percentage of CRT delivery and a percentage loss of CRT delivery by the respective IMD to the respective patient, wherein a sum of the percentage of CRT delivery and the percentage loss of CRT delivery equals approximately 100%.

2. The method of claim 1, wherein the cardiac rhythm event data comprises data indicative of at least one of atrial tachyarrhythmia, a premature ventricular contraction (PVC), or a ventricular sensing episode (VSE).

3. The method of claim 2, wherein the CRT performance data correlated to the cardiac rhythm event data comprises, for each patient in the first group of patients, the percentage loss of CRT delivery correlated to the at least one of atrial tachyarrhythmia, a PVC, or a VSE.

4. The method of claim 3, wherein the CRT performance data correlated to the at least one of AF, a PVC, or a VSE comprises, for each patient in the first group of patients, a percentage of the loss of CRT delivery that is due to each of atrial tachyarrhythmia, a PVC, a VSE, or other types of cardiac rhythm events.

5. The method of claim 4, wherein the CRT performance data correlated to the at least one of atrial tachyarrhythmia, a PVC, or a VSE comprises, for each patient in the first group of patients, a percentage of CRT delivery during atrial tachyarrhythmia.

6. The method of claim 5, further comprising collecting a set of CRT delivery parameters for each of the IMDs implanted within each patient in the first group of patients, wherein each set of CRT delivery parameters is associated with the CRT delivered by each of the IMDs to each of the patients, respectively.

7. The method of claim 6, further comprising collecting patient data for each patient in the first group of patients.

8. The method of claim 7, wherein aggregating, with the computing device, the CRT performance data correlated to the cardiac rhythm event data for the second group of patients comprises aggregating, with the computing device, at least one of the percentage of CRT delivery or the percentage loss of CRT delivery correlated to at least one of the patient data for each patient in the second group of patients, the percentage of CRT delivery during atrial tachyarrhythmia, the percentage of the loss of CRT delivery that is due to one or more of atrial tachyarrhythmia, a PVC, a VSE, or other types of cardiac rhythm events, or the set of CRT delivery parameters for each of the IMDs implanted within each patient in the second group of patients.

9. The method of claim 7, wherein aggregating, with the computing device, the CRT performance data correlated to the cardiac rhythm event data for the second group of patients comprises aggregating, with the computing device, the percentage of CRT delivery correlated to at least one of the patient data for each patient in the second group of patients, the percentage of CRT delivery during atrial tachyarrhythmia, or a time period over which atrial tachyarrhythmia occurred.

10. The method of claim 9, wherein the time period over which atrial tachyarrhythmia occurred is represented by a percentage of a total time over which the CRT performance data was generated.

11. The method of claim 7, wherein aggregating, with the computing device, the CRT performance data correlated to the cardiac rhythm event data for the second group of patients comprises aggregating, with the computing device, the patient data for each patient in the second group of patients correlated to the percentage of the loss of CRT delivery that is due to each of atrial tachyarrhythmia, a PVC, a VSE, and other types of cardiac rhythm events, and the set of CRT delivery parameters for each of the IMDs implanted within each patient in the second group of patients.

12. The method of claim 7, wherein aggregating, with the computing device, the CRT performance data correlated to the cardiac rhythm event data for the second group of patients comprises aggregating, with the computing device, the patients in the second group of patients by the percentage of CRT delivery by the respective IMD to the respective patient.

13. The method of claim 7, wherein aggregating, with the computing device, the CRT performance data correlated to the at least one cardiac rhythm event for the at least some of the IMDs comprises aggregating, with the computing device, the patients in the second group of patients by the percentage of CRT delivery during atrial tachyarrhythmia for all of the patients that experienced atrial tachyarrhythmia.

14. The method of claim 7, wherein aggregating, with the computing device, the CRT performance data correlated to the at least one cardiac rhythm event for the at least some of the IMDs comprises aggregating, with the computing device, the patients in the second group of patients by the percentage of the loss of CRT delivery that is due to one or more of atrial tachyarrhythmia, a PVC, a VSE, or other types of cardiac rhythm events.

15. The method of claim 7, wherein generating, with the computing device, the report comprises generating a report comprising at least one of an aggregation of patients by the percentage of CRT delivery by the respective IMD to the respective patient, an aggregation of patients by the percentage of CRT delivery during atrial tachyarrhythmia for patients that experienced atrial tachyarrhythmia, or an aggregation of patients by the percentage of the loss of CRT delivery that is due to one or more of atrial tachyarrhythmia, a PVC, a VSE, or other types of cardiac rhythm events.

16. A method comprising:
collecting cardiac resynchronization therapy (CRT) performance data correlated to cardiac rhythm event data for a first group of patients in which an implantable medical device (IMD) configured to deliver CRT is implanted;
aggregating, with a computing device, the CRT performance data correlated to the cardiac rhythm event data for a second group of patients from among the first group of patients; and
generating, with the computing device, a report comprising the aggregation of the CRT performance data correlated to the cardiac rhythm event data for the second group of patients, wherein generating, with the computing device, the report comprises generating a static electronic report comprising textual and graphical information representing the aggregation of the CRT performance data correlated to the cardiac rhythm event data for the second group of patients.

17. A method comprising:
collecting cardiac resynchronization therapy (CRT) performance data correlated to cardiac rhythm event data for a first group of patients in which an implantable medical device (IMD) configured to deliver CRT is implanted;
aggregating, with a computing device, the CRT performance data correlated to the cardiac rhythm event data for a second group of patients from among the first group of patients; and
generating, with the computing device, a report comprising the aggregation of the CRT performance data correlated to the cardiac rhythm event data for the second group of patients, wherein generating, with the computing device, the report comprises generating an interactive electronic report comprising textual and graphical information representing the aggregation of the CRT performance data correlated to the cardiac rhythm event data for the second group of patients.

18. A method comprising:
collecting cardiac resynchronization therapy (CRT) performance data correlated to cardiac rhythm event data for a first group of patients in which an implantable medical device (IMD) configured to deliver CRT is implanted;
aggregating, with a computing device, the CRT performance data correlated to the cardiac rhythm event data for a second group of patients from among the first group of patients; and
generating, with the computing device, a report comprising the aggregation of the CRT performance data correlated to the cardiac rhythm event data for the second group of patients, wherein aggregating, with the computing device, the CRT performance data correlated to the cardiac rhythm event data for the second group of patients comprises aggregating, with the computing device, the CRT performance data correlated to the cardiac rhythm event data for a group of patients from among the first group of patients that are treated at one location.

19. A method comprising:
collecting cardiac resynchronization therapy (CRT) performance data correlated to cardiac rhythm event data for a first group of patients in which an implantable medical device (IMD) configured to deliver CRT is implanted;
aggregating, with a computing device, the CRT performance data correlated to the cardiac rhythm event data for a second group of patients from among the first group of patients; and
generating, with the computing device, a report comprising the aggregation of the CRT performance data correlated to the cardiac rhythm event data for the second group of patients, wherein aggregating, with the computing device, the CRT performance data correlated to the cardiac rhythm event data for the second group of patients comprises aggregating, with the computing device, the CRT performance data correlated to the cardiac rhythm event data for a group of patients from among the first group of patients that are treated at multiple locations.

20. The method of claim 19, wherein the CRT performance data for each of the multiple locations is above a threshold level.

21. A system comprising:
at least one processor;
a computer-readable storage medium storing instructions, wherein the at least one processor is configured to execute the instructions stored on the computer-readable storage medium to cause the at least one processor to collect cardiac resynchronization therapy (CRT) performance data correlated to cardiac rhythm event data for a first group of patients in which an implantable medical device (IMD) configured to deliver CRT is implanted, aggregate the CRT performance data correlated to the cardiac rhythm event data for a second group of patients from among the first group of patients, and generate a report comprising the aggregation of the CRT performance data correlated to the cardiac rhythm event data for the second group of patients, wherein the CRT performance data for each patient in the first group of patients comprises a percentage of CRT delivery and a percentage loss of CRT delivery by the respective IMD to the respective patient, wherein a sum of the percentage of CRT delivery and the percentage loss of CRT delivery equals approximately 100%.

22. The system of claim 21, wherein the cardiac rhythm event data comprises data indicative of at least one of atrial tachyarrhythmia, a premature ventricular contraction (PVC), or a ventricular sensing episode (VSE).

23. The system of claim 22, wherein the CRT performance data correlated to the cardiac rhythm event data comprises, for each patient in the first group of patients, the percentage loss of CRT delivery correlated to the at least one of atrial tachyarrhythmia, a PVC, or a VSE.

24. The system of claim 22, wherein the CRT performance data correlated to the at least one of atrial tachyarrhythmia, a PVC, or a VSE comprises, for each patient in the first group of patients, a percentage of the loss of CRT delivery that is due to each of atrial tachyarrhythmia, a PVC, a VSE, or other types of cardiac rhythm events.

25. The system of claim 24, wherein the CRT performance data correlated to the at least one of atrial tachyarrhythmia, a PVC, or a VSE comprises, for each patient in the first group of patients, a percentage of CRT delivery during atrial tachyarrhythmia.

26. The system of claim 25, wherein the instructions stored on the computer-readable storage medium are configured to cause the at least one processor to collect a set of CRT delivery parameters for each of the IMDs implanted within each patient in the first group of patients, wherein each set of CRT delivery parameters is associated with the CRT delivered by each of the IMDs to each of the patients, respectively.

27. The system of claim 26, wherein the instructions stored on the computer-readable storage medium are configured to cause the at least one processor to collect patient data for each patient in the first group of patients.

28. The system of claim 27, wherein the instructions stored on the computer-readable storage medium are configured to cause the at least one processor to aggregate at least one of the percentage of CRT delivery or the percentage loss of CRT delivery correlated to at least one of the patient data for each patient in the second group of patients, the percentage of CRT delivery during atrial tachyarrhythmia, the percentage of the loss of CRT delivery that is due to one or more of atrial tachyarrhythmia, a PVC, a VSE, or other types of cardiac rhythm events, or the set of CRT delivery parameters for each of the IMDs implanted within each patient in the second group of patients.

29. The system of claim 27, wherein the instructions stored on the computer-readable storage medium are configured to cause the at least one processor to aggregate the percentage of CRT delivery correlated to at least one of the patient data for each patient in the second group of patients, the percentage of CRT delivery during atrial tachyarrhythmia, or a time period over which atrial tachyarrhythmia occurred.

30. The system of claim 27, wherein the instructions stored on the computer-readable storage medium are configured to cause the at least one processor to aggregate the patient data for each patient in the second group of patients correlated to the percentage of the loss of CRT delivery that is due to each of atrial tachyarrhythmia, a PVC, a VSE, and other types of cardiac rhythm events, and the set of CRT delivery parameters for each of the IMDs implanted within each patient in the second group of patients.

31. The system of claim 27, wherein the instructions stored on the computer-readable storage medium are configured to cause the at least one processor to aggregate the patients in the second group of patients by the percentage of CRT delivery by the respective IMD to the respective patient.

32. The system of claim 27, wherein the instructions stored on the computer-readable storage medium are configured to cause the at least one processor to aggregate the patients in the second group of patients by the percentage of CRT delivery during atrial tachyarrhythmia for all of the patients that experienced atrial tachyarrhythmia.

33. The system of claim 27, wherein the instructions stored on the computer-readable storage medium are configured to cause the at least one processor to aggregate the patients in the second group of patients by the percentage of the loss of CRT delivery that is due to one or more of atrial tachyarrhythmia, a PVC, a VSE, or other types of cardiac rhythm events.

34. The system of claim 27, wherein the instructions stored on the computer-readable storage medium are configured to cause the at least one processor to generate a report comprising at least one of an aggregation of patients by the percentage of CRT delivery by the respective IMD to the respective patient, an aggregation of patients by the percentage of CRT delivery during atrial tachyarrhythmia for patients that experienced atrial tachyarrhythmia, or an aggregation of patients by the percentage of the loss of CRT delivery that is due to one or more of atrial tachyarrhythmia, a PVC, a VSE, or other types of cardiac rhythm events.

* * * * *